United States Patent [19]

Down et al.

[11] Patent Number: 5,554,503
[45] Date of Patent: Sep. 10, 1996

US005554503A

[54] SAMPLE PROCESSING METHOD FOR *MYCOBACTERIUM TUBERCULOSIS*

[75] Inventors: James A. Down, Cary; Adriann H. Walters, Durham; Margaret S. Dey, Apex; Deborah R. Howard, Durham; Michael C. Little, Raleigh; William E. Keating, Durham, all of N.C.

[73] Assignee: Becton, Dickinson and Company, Franklin Lakes, N.J.

[21] Appl. No.: 286,100

[22] Filed: Aug. 4, 1994

Related U.S. Application Data

[63] Continuation of Ser. No. 60,844, May 11, 1993, abandoned.
[51] Int. Cl.$^6$ .............................. C12Q 1/68; C12P 19/34
[52] U.S. Cl. .............................. 435/6; 435/91.2; 935/77; 935/78
[58] Field of Search .............................. 435/6, 91.2, 238; 935/77, 78

[56] References Cited

U.S. PATENT DOCUMENTS

| | | | |
|---|---|---|---|
| 5,168,039 | 12/1992 | Crawford et al. | 435/6 |
| 5,270,184 | 12/1993 | Walker et al. | 435/91.2 |
| 5,376,527 | 12/1994 | Robson et al. | 435/6 |

FOREIGN PATENT DOCUMENTS

| | | |
|---|---|---|
| 0285439A2 | 10/1988 | European Pat. Off. . |
| 0395292A2 | 10/1990 | European Pat. Off. . |
| 0398677A3 | 11/1990 | European Pat. Off. . |
| 0428197A2 | 5/1991 | European Pat. Off. . |
| 0528306A2 | 2/1993 | European Pat. Off. . |
| WO91/03558 | 3/1991 | WIPO . |

OTHER PUBLICATIONS

V. Sritharan and R. H. Barker "A simple method for diagnosing *M. tuberculosis* infection in clinical samples using PCR" *Mol. Cell. Probes* 5:385–395 (1991).
A. H. J. Kolk, et al. "Detection of *Mycobacterium tuberculosis* in Clinincal Samples by Using Polymerase Chain Reaction and a Nonradioactive Detection System" *J. Clin. Microbiol.* 30:2567–2575 (1992).
R. M. Shawar, et al. "Detection of *Mycobacterium tuberculosis* in Clinical Samples by Two–Step Polymerase Chain Reaction and Nonisotopic Hybridization Methods" *J. Clin. Microbiol.* 31:61–65 (1993).
P. DelPortillo, et al. "Amplification of a Species–Specific DNA Fragment of *Mycobacterium tuberculosis* and Its Possible Use in Diagnosis" *J. Clin. Microbiol.* 29:2163–2168 (1991).
D. V. Cousins, et al. "Use of Polymerase Chain Reaction for Rapid Diagnosis of Tuberculosis" *J. Clin. Microbiol.* 30:255–258 (1992).
G. E. Buck, et al. "Rapid, Simple Method for Treating Clinical Specimens Containing *Mycobacterium tuberculosis* To Remove DNA for Polymerase Chain Reaction" *J. Clin. Microbiol.* 30:1331–1334 (1992).

T. Victor, et al. "Purification of Sputum Samples Through Sucrose Improves Detection of *Mycobacterium tuberculosis* by Polymerase Chain Reaction" *J. Clin. Microbiol.* 30:1514–1517 (1992).
P. Shankar, et al. "Rapid diagnosis of tuberculous meningitis by polymerase chain reaction" *Lancet* 337:5–7 (1991).
D. DeWit, et al. "Direct Detection of *Mycobacterium tuberculosis* in Clinical Specimens by DNA Amplification" 28:2437–2441 (1990).
C. Pierre, et al. "Use of Reamplification Protocol Improves Sensitivity of Detection of *Mycobacterium tuberculosis* in Clinical Samples by Amplification of DNA" *J. Clin. Microbiol.* 29:712–717 (1991).
D. Thierry, et al. "The detection of *Mycobacterium tuberculosis* in uncultured clinical specimens using the polymerase chain reaction and a non–radioactive DNA probe" *Molec. Cell. Probes* 6:181–191 (1992).
A. Brisson–Noel, et al. "Rapid Diagnosis of Tuberculosis by Amplification of Mycobacterial DNA in Clinical Samples" *Lancet* Nov. 4, 1989:1069–1071.
B. B. Plikaytis, et al. "Differentiation of *Mycobacterium tuberculosis* and *Mycobacterium bovis* BCG by a polymerase chain reaction assay" *Molec. Cell. Probes* 5:215–219 (1991).
K. D. Eisenach, et al. "Detection of *Mycobacterium tuberculosis* in Sputum Samples Using a Polymerase Chain Reaction" *Am. Rev. Respir. Dis.* 144:1160–1163 (1991).
G. Rahav, et al. "Development of sensitive methods for the detection of mycobacteria by DNA probes" *FEMS Microbiol. Lett.* 72:29–34 (1990).
L. G. Wayne and W. M. Gross "Isolation of Deoxyribonucleic Acid from Mycobacteria" *J. Bacteriol.* 95:1481–1482 (1968).
E. B. Hill, et al. "Purification of Mycobacterial Deoxyribonucleic Acid" *J. Bacteriol.* 112:1033–1039 (1972).
I. Baess "Isolation and Purification of Deoxyribonucleic Acid from Mycobacteria" *Acta Path. Microbiol. Scand. Sect.* B, 82:780–784 (1974).
J. W. U. Fries, et al. "Detection of Untreated Mycobacteria by Using Polymerase Chain Reaction and Specific DNA Probes" *J. Clin. Microbiol.* 29:1744–1747 (1991).

(List continued on next page.)

*Primary Examiner*—Stephanie W. Zitomer
*Attorney, Agent, or Firm*—Donna R. Fugit

[57] ABSTRACT

Methods for processing samples which may contain mycobacteria which are compatible with both conventional culturing techniques and nucleic acid analysis. It has been found that the harsh chemical treatment previously thought necessary to obtain efficient lysis can be eliminated without loss of lysis efficiency, thereby eliminating reagents which may inhibit subsequent nucleic acid-based reactions. Heat alone is sufficient to lyse mycobacteria, even in buffers which do not contain detergents, chelators, enzymes, etc. Residual reagents introduced by conventional sample processing methods for culture can be successfully removed from the processed pellet without significant loss of microorganisms by at least two washings with saline, water, or buffers compatible with nucleic acid analysis and appropriate centrifugation.

15 Claims, No Drawings

OTHER PUBLICATIONS

U. Sjobring, et al. "Polymerase Chain Reaction for Detection of *Mycobacterium tuberculosis*" *J. Clin. Microbiol.* 28:2200–2204 (1990).

R. J. Patel, et al. "Sequence Analysis and Amplification by Polymerase Chain Reaction of a Cloned DNA Fragment for Identification of *Mycobacterium tuberculosis*" *J. Clin. Microbiol.* 28:513–518 (1990).

C. Hackel, et al. "Specific identification of *Mycobacterium leprae* by the polymerase chain reaction" *Molec. Cell. Probes* 4:205–210 (1990).

A. Brisson–Noel, et al. "Diagnosis of tuberculosis by DNA amplification in clinical practice evaluation" *Lancet* 338:364–366 (1991).

K. D. Eisenach, et al. "Polymerase Chain Reaction Amplification of a Repetitive DNA Sequence Specific for *Mycobacterium tuberculosis*" J. Infect. Dis. 161:977–981 (1990).

K. D. Evans, et al. "Identification of *Mycobacterium tuberculosis* and *Mycobacterium avium–M. intracellulare* Directly from Primary BACTEC Cultures by Using Acridinium–Ester–Labeled DNA Probes" *J. Clin. Microbiol.* 30:2427–2431 (1992).

Kocagöz et al. J. Clin. Micro. 31(6):1435–1438 (1993).

Walker et al. Nuc. Acids Res. 20(7):1691–1696 (1992).

Walker et al. P.N.A.S. 89:392–396 (1992).

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /standard_name="5'Biotin label"
            / label=5'-BBB- ( x i ) SEQUENCE DESCRIPTION: SEQ ID NO:1:

GCTTTGCTAG TTGCC 15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 15
        ( D ) OTHER INFORMATION: /standard_name="3'amine
            conjugated to alkaline phosphatase"
            / label=-al2-AP-3'

( x i ) SEQUENCE DESCRIPTION: SEQ ID NO:2:

TCAGACATCG TCGCT 15

( 2 ) INFORMATION FOR SEQ ID NO:3:

-continued

```
( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_feature
    ( B ) LOCATION: 1
    ( D ) OTHER INFORMATION: /standard_name="5'Biotin label"
            / label=5'-BBB- ( x i ) SEQUENCE DESCRIPTION: SEQ ID NO:3:

CCTGAAAGAC GTTAT                                                      15

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 16
        ( D ) OTHER INFORMATION: /phenotype="3'AMINE CONJUGATED TO
                ALKALINE PHOSPHATASE"
                / label=-am-AP-3'

( x i ) SEQUENCE DESCRIPTION: SEQ ID NO:4:

CCACCATACG GATAGT                                                     16

( 2 ) INFORMATION FOR SEQ ID NO:5:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ACTGAGATCC CCTAGCGACG ATGTCTGAGG CAACTAGCAA AGCTGGTCGA GTACGCC        57

( 2 ) INFORMATION FOR SEQ ID NO:6:

( i ) SEQUENCE CHARACTERISTICS:
        ( A ) LENGTH: 52 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( x i ) SEQUENCE DESCRIPTION: SEQ ID NO:6:

ACTGAGATCC CCTATCCGTA TGGTGGATAA CGTCTTTCAG GTCGAGTACG CC             52
```

SAMPLE PROCESSING METHOD FOR *MYCOBACTERIUM TUBERCULOSIS*

This application is a continuation of application Ser. No. 08/060,844, filed May 11, 1993.

FIELD OF THE INVENTION

The present invention relates to methods for releasing nucleic acids from microorganisms. In particular the invention relates to such methods which are compatible with subsequent manipulations of the nucleic acids, for example nucleic acid amplification.

BACKGROUND OF THE INVENTION

Mycobacterium sp. are conventionally identified by microbiological culture. As these microorganisms are slow growing and may exist in low numbers in clinical samples, such culturing techniques are time consuming and may require three to six weeks of culturing before a result is available. *Mycobacterium tuberculosis* (M.tb) is the causative agent of tuberculosis in humans and is currently diagnosed using these conventional culturing techniques. To prepare for M.tb culture, sputum samples are processed by methods which have been in use for about thirty years (G. Kubica, et al. 1963. Am. Rev. Resp. Dis. 87:775–779). These and other sample processing methods for M.tb culture have been developed for the purposes of 1) reducing the viscosity of the sputum sample to facilitate handling, 2) killing contaminating organisms (such as fungi and non-mycobacteria) to prevent co-culturing with *M. tuberculosis* and confusion of the diagnosis, and 3) concentrating the sample into a small volume for seeding cultures. To accomplish these goals, conventional sample preparation methods for Mycobacteria sp. have traditionally employed harsh conditions and caustic, toxic or reactive reagents. Conventional sample processing procedures for mycobacterial culture are reviewed by G. Kubica in *The Mycobacteria: A Source Book. Part A*. (Kubica, G. and Wayne, L. eds.) Marcel Dekker, N.Y. (1984).

A commonly used sample processing method for M.tb culture is the N-acetyl-L-cysteine/sodium hydroxide method. This method uses NaOH, sodium citrate and N-acetyl L-cysteine (NALC) to digest the sample, with recovery of the mycobacteria by centrifugation. The pellet is then resuspended in a small volume and used to inoculate the culture medium. Similar methods have been developed in which sodium hydroxide is used alone, with neutralization of the pellet prior to resuspension and culturing. NaOH has also been used with sodium lauryl sulfate (SLS) to process samples for culture, again with neutralization of the pellet by addition of acid prior to inoculation of the culture medium. The ZEPHIRAN-trisodium phosphate method for sample processing uses trisodium phosphate and ZEPHIRAN (benzalkonium chloride) in a similar process.

Nucleic acid-based genetic methods for identification of microorganisms have greatly reduced the time and labor involved in clinical diagnosis. Such methods include, for example, nucleic acid hybridization (e.g., Southern and slot blots), nucleotide sequencing, nucleic acid cloning techniques, restriction digestion of nucleic acids and nucleic acid amplification. In particular, nucleic acid amplification has provided means for rapid, sensitive and specific identification of microorganisms by amplification and detection of specific genes or gene fragments. However, sample processing for these nucleic acid analyses requires different criteria than sample processing for culturing: 1) nucleic acids must be released from the microorganism in a form suitable for the analysis, 2) nucleic acids must be present in a composition with the appropriate components, ionic strength and pH for the analysis reactions, and 3) inhibitors of the reactions, if present, must be removed. For nucleic acid amplification, certain inhibitors are known to be present in the sample itself, e.g., heme and polysaccharides. In addition, disinfection of the sample is of particular concern for M.tb nucleic acid-based analyses, as such tests are generally not performed in a biosafety cabinet in clinical laboratories.

At the present time nucleic acid-based methods for diagnosis and identification of mycobacteria do not completely replace conventional culturing, as samples which are positive by these methods are generally cultured to determine drug sensitivity. In addition, at the present time the results of nucleic acid analyses are often verified by culture. The need for both conventional culturing and genetic analysis from a single sample has demonstrated that conventional M.tb sample processing for culture is a source of inhibitors which interfere with subsequent nucleic acid-based reactions, particularly amplification. Conventional sample processing for culture is therefore incompatible with many nucleic acid analyses, especially nucleic acid amplification. This incompatibility is believed to be due to the harsh chemical treatment (NaOH, benzalkonium chloride, etc.), which may inhibit the enzymes involved in amplification or render the nucleic acid unamplifiable by other means. Ethylenediamine tetraacetate (EDTA) and lytic enzymes customarily used to release nucleic acids from microorganisms are similarly inhibitory. The conventional phenol/chloroform extraction methods for removing inhibitors may leave traces of these reagents, which are also inhibitory. In addition, residual chaotropes, alcohol or silica, which are conventionally used for purification of nucleic acids may inhibit nucleic acid amplification reactions. The presence of such inhibitors in samples processed by conventional methods has limited the volume of processed sample which can be amplified. That is, to ensure sufficient dilution of inhibitors, only small aliquots (usually less than about 10 μl) of such samples could previously be added to an amplification reaction. Sample volumes above about 10 μl produced erratic results or amplification failures. Even amplification of less than 10 μl of conventionally processed samples have produced erratic results in amplification reactions due to the presence of inhibitors introduced by sample processing. In addition, Applicants have observed that TRITON and other detergents inhibit solid phase assays for detection of amplified DNA.

The ideal sample processing method for nucleic acid amplification of M.tb therefore has the following components: 1) removal of amplification inhibitors, in particular those introduced by sample processing for culture, 2) release from the M.tb of a sufficient amount of DNA for amplification, and 3) disinfection of the sample. Others have attempted to remove amplification inhibitors introduced by conventional M.tb sample processing for culture. Most commonly, these methods involve washing the pellet obtained from sample processing for culture, but sufficient washing to remove inhibitors risks loss of the M.tb organisms with subsequent variability and inaccuracy in culturing results. V. Sritharin and R. Barker (1991. M. Cell. Probes 5:385–395.), A. J. H. Kolk, et al. (1992. J. Clin. Micro. 30:2567–2575.), R. M. Shawar, et al. (1993. J. Clin. Micro. 31:61–65.), P. DelPortillo, et al. (1991. J. Clin. Micro. 29:2163–2168.), and D. V. Cousins, et al. (1992. J. Clin. Micro. 30:255–258.) describe centrifugation washing of a portion of an NALC pellet in specialized lysis buffers containing detergent and/or ethylenediamine tetraacetate (EDTA) and/or lytic enzymes. Shawar, et al. used one washing/centrifugation step. While G. E. Buck, et al. (1992. J. Clin. Micro. 30:1331–1334.) used two microcentrifuge washes of NALC pellets in phosphate-buffered saline, this method was described as having low efficiency and was abandoned. The low efficiency was probably due to inefficient lysis, which was accomplished by either 1) 1–12 hr. at 55° C. in a lysis buffer containing enzymes and TRITON, or 2) eight cycles of freezing and thawing. Kolk, et al. also used two washes, but the washes were with lysis buffer which contained detergent and lysis was by exposure to 60° C. for 18 hr. These authors noted failures in their PCR reactions thereafter, and these samples were further treated with phenol/chloroform extraction. T. Victor, et al. (1992. J. Clin. Micro. 30:1514–1517.) described a variation of the washing protocols in which a portion of an NALC pellet was recentrifuged through a sucrose solution. In addition to being time consuming and inconvenient, this method resulted in a 100 fold decrease in sensitivity which would be unacceptable for a diagnostic test.

Other practitioners have attempted to remove amplification inhibitors from samples processed for culture by classical extraction methods using phenol and/or chloroform. These include Cousins, et al. and DelPortillo, et al., supra, as well as P. Shankar, et al. (1991. Lancet 33:5–7.), D. DeWit, et al. (1990. J. Clin. Micro. 28:2437–2441.), C. Pierre, et al. (1991. J. Clin. Micro. 29:712–717.), D. Thierry, et al. (1992. Mol. Cell. Probes 6:181–191.) and A. Brisson-Noel, et al. (1989. Lancet Nov. 4:1069–1071). These methods may not remove all inhibitors and traces of phenol and/or chloroform can contaminate the sample after extraction and inhibit amplification. In addition, these reagents are caustic, flammable and toxic. Commercially-available DNA purification kits (e.g., GENE CLEAN) have also been used to purify M.tb DNA from samples conventionally processed for culture (B. B. Plikaytis, et al. 1991. Mol. Cell. Probes 5:215–219.; K. D. Eisenach, et al. 1991. Am. Rev. Respir. Dis. 144:1160–1163.). This is a time-consuming and cumbersome process which involves many steps and employs a caustic chaotropic binding buffer. Applicants have tested the GENECLEAN method and have found that the sensitivity of subsequent PCR reactions was reduced, most likely because the recovery of M.tb DNA by the GENECLEAN kit was less than recovery using the present method.

Conventional nucleic acid-releasing protocols for mycobacteria have employed enzymatic digestion (Kolk, et al., Cousins, et al., DelPortillo, et al. and Buck, et al., supra), freeze-thaw treatment in detergent-containing buffers (Buck, et al., supra), detergent extraction (DeWit, et al., supra), sonication or shearing in detergent and/or enzyme containing buffers (Buck, et al. and Savic, et at., supra) or combinations of these techniques (Plikaytis, et al. and Eisenach, et al., supra). As stated above, the detergents, enzymes and EDTA employed in these methods are potential inhibitors of subsequent nucleic acid amplification reactions. Heat has also previously been used to induce lysis of mycobacteria, but again these methods employed lysis in buffers which contained EDTA, detergent and/or lytic enzymes (Sritharin and Barker, Shawar, et al. and Buck, et al., supra) because it was believed that heat alone would not be sufficient to promote efficient lysis. Additional reagents have therefore been customarily used in conjunction with heat to promote efficient lysis.

SUMMARY OF THE INVENTION

The present invention provides methods for processing samples which may contain mycobacteria which are compatible with both conventional culturing techniques and nucleic acid analysis. It has unexpectedly been found that the harsh chemical treatment previously thought necessary to obtain efficient lysis of the microorganisms can be eliminated without loss of lysis efficiency, thereby eliminating reagents which may inhibit subsequent nucleic acid-based reactions. Heating for at least 5 min. at about 95°–120° C. in water, saline or a buffer compatible with the selected nucleic acid analysis not only provides highly efficient lysis of mycobacteria (essentially 100%), but also disinfects the sample. It has further unexpectedly been found that potentially inhibitory reagents used in conventional sample processing methods for culture (i.e., liquification and decontamination) can be successfully removed from the processed pellet without significant loss of microorganisms by at least two washings with saline, water or a buffer compatible with the nucleic acid analysis (i.e., without detergents, enzymes, EDTA, etc.) and centrifugation at a speed sufficient to produce a tight pellet which minimizes loss of material during the washing steps.

The inventive methods therefore allow culturing and nucleic acid analysis to be performed on a sample without the need for separate sample processing protocols. The present methods are simpler, faster and more reproducible than previous methods and do not require any specialized equipment. Further, they employ inexpensive and readily available reagents, none of which require special handling. As the samples are simultaneously disinfected in the lysis procedure, biohazards are eliminated and the small sample size reduces biological waste. Unlike previous methods, in which the volume of sample which could be analyzed was often limited by the presence of inhibitors, relatively large volumes of samples processed by the inventive methods (up to 75% of amplification reaction volume) can be amplified reproducibly and without loss of sensitivity. The ability to amplify large volumes allows the practitioner to detect rare target sequences which may be missed when a small aliquot of a sample must be amplified to avoid interference from inhibitors.

DETAILED DESCRIPTION OF THE INVENTION

The instant invention provides methods for processing samples for detection and identification of Mycobacteria sp. which are compatible with both culture and nucleic acid-based analysis, including nucleic acid hybridization, restriction digestion, nucleotide sequencing, and nucleic acid amplification. The present methods are compatible with a variety of nucleic acid-based reactions because, in contrast to previously known sample processing methods, no toxic or inhibitory reagents are used for release of nucleic acids. Potentially toxic or inhibitory substances employed for liquification and decontamination of the sample are efficiently removed. The present methods are therefore compatible with any protocol for analysis and detection of nucleic acid which is sensitive to inhibition by the detergents, enzymes, chelators, chaotropes and solvents previously used for sample processing.

A sample, usually a clinical sample such as sputum, is first processed by conventional procedures for liquification and decontamination (i.e., killing of non-mycobacteria) as described above. Any of the known liquification/decontamination procedures are suitable for this step, including the NALC, ZEPHIRAN-trisodium phosphate, NaOH and SLS procedures for recovering mycobacteria from a sample, as reviewed by Kubica, 1984, supra. The NALC procedure is preferred because it is compatible with automated culturing instruments such as the BACTEC instruments commercially available from Becton, Dickinson Diagnostic Instrument Systems, Sparks, Md. For use with the BACTEC instrument, the sample is mixed with an equal volume of liquification solution (2% NaOH, 1.45% sodium citrate, 0.5% N-acetyl L-cysteine) and incubated for 15–20 min. at room temperature. Neutralization solution (0.068 M sodium and potassium phosphate) is then added to a volume of 50 ml and the sample is centrifuged at 4° C. for 15–20 min. at 4,000 xg. The supernatant is discarded. This process concentrates any organisms present in the sample into a small volume NALC pellet (less than 1 ml.). In conventional culturing methods, the NALC pellet is resuspended in 1.5–2 ml of an appropriate buffer or water for seeding solid or liquid growth media.

To prepare the sample for nucleic acid analysis, the liquified/decontaminated pellet is then processed to release nucleic acids for detection and analysis. If only nucleic acid-based procedures are to be performed, the entire pellet may be processed. It is preferred, however, that only a portion of the pellet be processed further, allowing both culturing and nucleic acid analysis to be performed on a single sample. In one embodiment, the final pellet from the liquification process may be split and a portion used for culture and a portion processed for nucleic acid analysis. Alternatively, the liquified sample may be split, with one portion being centrifuged and the pellet processed for culture and the other portion being centrifuged and the pellet processed for nucleic acid analysis. The liquified/decontaminated pellet for nucleic acid analysis is then washed to remove inhibitory, caustic and toxic reagents which may interfere with the subsequent nucleic acid analysis. The wash solution may be saline, water or a physiological buffer (e.g., phosphate or Tris buffer) and does not contain detergents, enzymes, chelating agents (e.g., EDTA) or other reagents which may inhibit subsequent nucleic acid analysis and detection. Preferably, the wash solution is similar to the buffer used in the subsequent nucleic acid analysis. For example, if the nucleic acid is to be hybridized to a probe or sequenced, the wash solution may be the hybridization or sequencing buffer. If the nucleic acid is to be amplified, the wash solution may be a buffer appropriate for the selected nucleic acid amplification reaction. SDA is preferred for amplification of nucleic acids released according to the invention, and 0.025 M potassium phosphate, pH 7.6 is therefore a preferred wash solution as this buffer is customarily employed in SDA reactions.

In one embodiment, the pellet is washed in a relatively large volume of wash solution, for example, up to about 20 ml. After mixing the pellet with the wash solution, the sample is centrifuged at a minimum of about 4,000 xg to produce a tight pellet which is resistant to loss of material upon further handling. This is preferably accomplished using a standard clinical centrifuge, centrifuging the sample for at least 5 min. and preferably at least 15 min. The supernatant is discarded and the pellet is resuspended in a second volume (generally up to about 20 ml) of wash solution. The sample is centrifuged a second time (at least 4,000 xg) to form a pellet and the supernatant is discarded.

In a second embodiment, the wash solution volume is kept small for ease of sample handling. This has the advantage of reducing the volume of potentially biohazardous material which must be disposed of and allows the procedure to be easily performed in a biological safety cabinet. After mixing the liquified/decontaminated pellet with about 1 ml of the wash solution, the sample is centrifuged at a minimum of 12,000 xg to produce a tight pellet and prevent loss of material upon further handling. Centrifugation will generally be for at least 1 min., preferably at least 5 min. In a preferred embodiment, approximately one quarter of the pellet is transferred to a small tube and mixed with the 1 ml of wash solution. As the volume of the sample is small, centrifugation is preferably accomplished in a microcentrifuge for convenience in the laboratory and to allow centrifugation in a biological safety cabinet or hood. The supernatant is discarded and 1 ml of wash solution is added a second time and mixed with the pellet. The sample is again centrifuged (at least 12,000 x g) to form a pellet and the supernatant is discarded.

For either the clinical centrifuge or the microcentrifuge method, two washes are the minimum required for successful removal of inhibitors. Optionally, additional washes may be employed as long as the sample is centrifuged at a high enough speed to form a tight pellet that is resistant to loss of material when the supernatant is removed.

After washing, any mycobacteria which are present in the pellet are lysed as follows. At least about 100 µl, preferably about 1 ml, of the appropriate buffer for the desired nucleic acid analysis (e.g., hybridization buffer, sequencing buffer, amplification buffer) is added to the pellet and the sample is heated at about 95°–120° C. for a period of time sufficient to cause lysis of mycobacteria. Preferably, the sample is heated for at least 5 min., preferably 15–30 min., most preferably 30 min. Heating may be accomplished by autoclaving, or placing the tube in a boiling water bath or a forced air convection oven. The boiling water bath is the preferred method, as lysis by this method appears to be associated with improved reproducibility in subsequent SDA reactions. Heating blocks, while resulting in sufficient lysis for nucleic acid analysis, may not reliably produce disinfection (i.e., 100% lysis) because of delayed or inefficient heat transfer from the block to the sample. After heating, the sample may be used directly in the nucleic acid analysis or detection protocol or, optionally, filtered or centrifuged to remove debris. The sample is preferably centrifuged briefly in a microcentrifuge (approximately 10 sec.) to remove debris prior to nucleic acid amplification.

The released nucleic acid in the lysed sample may then be used in the selected nucleic acid analysis or detection protocol without further treatment, as no toxic and inhibitory reagents are introduced by the lysing protocol and the sample may be lysed in the buffer appropriate for the analysis. Nucleic acids prepared according to the invention are compatible with any of the known nucleic acid analysis and detection protocols. These include, but are not limited to, nucleic acid hybridizations (e.g., Southern blots, slot blots), restriction digestion and cloning, nucleotide sequencing and nucleic acid amplification. Such protocols are well known in the art and are reviewed in *Molecular Cloning: A Laboratory Manual*, Second Edition, by J. Sambrook, E. F. Fritsch and T. Maniatis, Cold Spring Harbor Laboratory Press, 1989. The present sample processing methods are particularly useful for amplification of nucleic acids because elimination of inhibitors enhances sensitivity of diagnostic tests and allows the practitioner to amplify a larger volume of the nucleic acid preparation than was previously possible. A target sequence which is extremely rare is therefore more likely to be represented in the aliquot of sample amplified, improving the accuracy and reliability of the amplification result.

Certain steps of the present methods have been found to be particularly important to its success. First, the liquified/ decontaminated pellet must be washed at least twice with a minimum of 1 ml of wash solution each time to effectively remove the toxic and inhibitory reagents used in the liquification. A single washing step is not sufficient for processing some samples. Larger volumes of wash solution, if feasible, result in even more efficient removal of these reagents. Second, the washed sample must be centrifuged so as to form a pellet which will remain intact during removal of the supernatant and re-washing. Third, it was not previously known or appreciated in the art that efficient heat lysis could be accomplished without the use of detergents, enzymes or chelating agents. These reagents were previously thought to be essential because heat alone was not believed to be sufficient to lyse mycobacteria. While certain previously known heat lysis protocols employ a relatively brief exposure to very high temperature, all add additional potentially inhibitory substances to enhance lysis, as described above. In contrast, the present invention for the first time demonstrates that heating at 95°–120° C. is sufficient by itself to produce essentially 100% lysis of mycobacteria. This discovery further permits the sample to be simultaneously lysed and disinfected.

The following experimental examples are provided to illustrate certain embodiments of the invention, but are not to be construed as limiting the invention and its equivalents as defined by the appended claims.

EXAMPLE 1

Two methods of liquification and different washing conditions using a clinical centrifuge were tested for their ability to remove inhibitors to SDA amplification. The two liquification protocols were 1) the method recommended by BACTEC and 2) 0.5N sodium hydroxide containing 0.1M sodium titrate and 1% NALC as described by Kubica, 1963, supra. The BACTEC method uses half the concentration of NALC of method 2. For each liquification method, washing the pellet with two or three 20 ml washes prior to amplification were compared. Five tuberculosis (TB)-negative sputum samples were pooled. Eight aliquots of 5 ml each were pipetted into 50 ml disposable tubes. These were negative controls. The remaining pooled sample volume was split into two approximately equal portions. A single TB-positive sputum sample was then split into each of the two TB-negative sample portions to make two TB-positive pools ("A" and "B"). This allowed the creation of a relatively homogeneous TB-positive pooled sample with a low number of M.tb relative to a typical positive sample.

Pool A was liquified by addition of an equal volume of 2% NaOH/1.45% citrate/0.5% NALC and vortexing for 1 min. The sample was then aliquoted equally into eight 50 ml disposable tubes. Four of the TB-negative samples were liquified in the same way. Aliquots were incubated for 20 min. at room temperature, then neutralized by addition of neutralizing buffer to a volume of 50 ml. The aliquots were then centrifuged for 20 min. at 4,200 x g in a clinical centrifuge. The supernatant was discarded and the pellets were washed by addition of 20 ml of 25 mM KPO$_4$ and centrifuging for 5 min. Either two or three washes were performed in identical fashion, and the resulting washed pellet was pipetted into a 1.5 ml disposable screw-cap tube.

Pool B was liquified by addition of an equal volume of 0.5N NaOH/0.1M citrate/1% NALC. Four of the TB-negative samples were liquified in the same way. The positive pool was split into eight aliquots as above and incubated for 15 min. at room temperature. Following incubation, each aliquot was brought to 50 ml with 25 mM KPO4, pH 7.6, and centrifuged for 15 min. at 4,200 x g in a clinical centrifuge. The resulting pellets were washed two or three times as for Pool A and the washed pellets were also put into 1.5 ml tubes. All aliquots from both pools and the negative samples were autoclaved for 15 min., microfuged for about 1 min. to remove debris and the supernatants were subjected to SDA amplification of the M.tb IS6110 sequence essentially as described by G. T. Walker, et al. (1992. Nuc. Acids Res. 20:1691–1696; 1992. Proc. Natl. Acad. Sci. 89:392–396). Twenty-five µl and 2.5 µl portions of each aliquot were amplified. The amplification reactions further included a known amount of an internal control sequence, the amplification of which served as an internal control for amplification efficiency. Twenty-five thousand copies of the control sequence molecule (SEQ ID NO:5)

5'      ACTGAGATCCCCTAGCGACGATGTCT-GAGGCAACTAGCAAAGCTGGTCGAGTACGCC 3' were added to each aliquot of sample with the SDA reaction mixture and were co-amplified with the M.tb target sequence (SEQ ID NO:6)

5'      ACTGAGATCCCCTATCCGTATGGTG-GATAACGTCTTTCAGGTCGAGTACGCC 3'.

using a single set of amplification primers.

Amplification products were detected in the following chemiluminescent DNA probe assay. Oligonucleotide capture probes were synthesized using a DNA synthesizer (Model 380B, Applied Biosystems, Foster City, Calif.) and BIOTIN-ON Phosphoramidite (Clonetech, Palo Alto, Calif.). This resulted in three biotin residues at the 5'terminus of the capture probe. The capture probe for the control sequence (SEQ ID NO:1) was 5'-GCTTTGCTAGTTGCC3' and the capture probe for the Mtb IS6110 target sequence (SEQ ID NO:3) was 5'CCTGAAAGACGTTAT- 3'. The oligoncleotides were purified by reverse phase High Pressure Liquid Chromatography (HPLC) (Brownlee Lab Aquapore RP 300 Column- 220 X 4.6 mm, C8 column, 7 particle, 300 Å pore size) with a UV monitor at 254 mn and a gradient of 14–44% Buffer B in Buffer A over one hour (Buffer B: 0.1M triethylamine-acetate, pH 7 with 50% acetonitrile; Buffer A: 0.1M triethylamine-acetate, pH 7) and a flow rate of 1 ml/min.

The oligodeoxynucleotide detector probes were synthesized using the Model 380B DNA synthesizer and a 3'-amino-modifier-C3 column (Glenn Research, Sterling, Va.). This produced oligonucleotides with a 3' amine terminus for subsequent conjugation to alkaline phosphatase. The detector probe for the control sequence (SEQ ID NO:2) was 5'-TCAGACATCGTCGCT-al$_2$-AP- 3' (al$_2$=amino link 2). The detector probe for the IS6110 target sequence (SEQ ID NO:4) was 5'-CCACCATACGGATAGT-am-AP-3' (am= amino modifier). Calf intestine alkaline phosphatase (AP) (EIA grade, Boehringer Mannheim, Indianapolis, Ind.) was dialyzed overnight at 4° C. against 50 mM potassium phosphate pH 7.5 and subsequently centrifuged to remove aggregates. Four ml of 10 mg/ml AP was combined with 40 µl of 50 mM succinimidyl-4-(p-maleimidophenyl) butyrate (SMPB) (Pierce, Rockford, Ill.) dissolved in N,N'-dimethylformamide (DMF) (Aldrich, Milwaukee, Wis.) and allowed to react in the dark at room temperature for 30 min. The derivatized AP and excess SMPB were separated using a NAP-25 column (Pharmacia) and 50 mM potassium phosphate pH 7.5 (degassed and purged with N$_2$). The absorbances of the NAP-25 column fractions were read at 260 and 280 nm and the void volume peak was pooled. The concentration of derivatized alkaline phosphatase was determined by absorbance at 280 nm using an extinction coefficient of 0 m75 ml/μmole cm$^{-1}$. The derivatized AP obtained was stored on ice less than two hours until conjugation to the derivatized oligodeoxynucleotides.

Fifty nmoles of oligodeoxynucleotide was diluted in 13.4 μl 1M potassium phosphate pH 7.2 and mixed with 26.8 gl of 50 mM n-succinimidyl-3-(2-pyridyldithio)propionate (SPDP) (Pierce, Rockford, Ill.) diluted in DMF. This mixture was incubated in the dark for 1 hr. at room temperature. Dithiothreitol (DTT) was diluted in 50 mM potassium phosphate pH 7.5 to a concentration of 1M and added to the oligodeoxynucleotide/DMF mixture to a final concentration of 0.1M and allowed to incubate for 15 min. at room temperature. Excess DTT and SPDP were separated from the derivatized oligodeoxynucleotide by elution over a NAP-25 column with 50 mM potassium phosphate pH 7.5 (degassed and purged with $N_{217}$). The derivatized oligodeoxynucleotide eluted in the void volume as judged by absorbance at 160 and 180 nm. The reduced oligodeoxynucleotide, in order to avoid oxidation, was reacted with the derivatized AP within 10 min. The derivatized oligodeoxynucleotide and derivatized AP were incubated 1–4 hrs. at room temperature and then overnight at 4° C. The solution was quenched using 1/100th volume of 50 mM beta-mercaptoethanol in 50 mM potassium phosphate pH 7.5. The crude conjugate was concentrated according to the manufacturer's instructions using CENTRIPREP 30 (Amicon) to approximately 2 ml using 20 mM Tris pH 7.5. The crude conjugate was purified by HPLC using a DEAE-5PW column (7.5 mm×7.5 cm) and a gradient of 0 to 66% Buffer B in Buffer A (Buffer B: 20 mM Tris, 1M NaCl pH 7.5; Buffer A: 20 mM Tris pH 7.5) and a flow rate of 1 ml/min. Absorbance was monitored at 254 nm. The absorbance at $A_{260}$ and $A_{280}$ nm were taken using a spectrophotometer and the fractions with $A_{260}/A_{280}$ equal to 1 were pooled. The protein concentration of the conjugated oligodeoxynucleotide was determined (BCA Protein Assay Kit, Pierce, Rockford, Ill.).

The activity of the alkaline phosphatase (AP) detector oligodeoxynucleotide probes was determined as follows. The conjugate was diluted to 5 μg/ml in 50 mM Tris-HCl, 100 mM NaCl, 1 mM $MgCl_2$, 1 mg/ml BSA, pH 7.5. The substrate, 4-nitrophenylphosphate (pNPP), at a concentration of 5 mM, was prepared in 1 M diethanolamine, 1 mM $MgCl_2$, pH 9.8. AP activity was assayed as follows, at 25° C. The conjugate (5 μl) was pipetted into 2 ml of the substrate solution and the change in absorbance was monitored at 405 nm. The initial rate was calculated from the linear region, and the reaction rate (μmole product/minute) was calculated using the extinction coefficient of the product p-nitrophenol at 405 nm as equal to 18500 $M^{-1}cm^{-1}$. The specific activity of the AP detector oligodeoxynucleotide was calculated in μmole/minute/mg. The AP detector probe was diluted to 2 μM in 20 mM Tris pH 7.5, 1M NaCl, 50 μg/ml sonicated salmon sperm DNA, 0.05% sodium azide, and stored thereafter at 4° C. The 20 mM Tris, pH 7.5, 1M NaCl buffer was autoclaved before addition of the other components.

Coated microtiter plates for capture of the target/probe complexes were prepared as follows. Biotinylated bovine serum albumin (biotin*BSA) (Pierce, Rockford, Ill.) was diluted to 5 μg/ml in 0.3M glycine pH 9.6 (prepared using autoclaved water) and was pipetted into each well (200 μl/well) of a MICROLITE1 plate (Dynatech, Chantilly, Va.). The plates were incubated at 4° C. overnight and washed twice (375 μl/wash) using FTA hemagglutination buffer (Becton Dickinson Microbiology Systems) pH 7.2 prepared using autoclaved water. Streptavidin (50 μg/ml) (BRL, Bethesda, Md.) in hemagglutination buffer was added to the biotin*BSA coated microtiter wells (100 μl/well). Plates were covered and incubated for 1 hr. at 37° C. Unbound streptavidin was discarded by inversion and manual shaking. Blocking buffer (300 μl/well) (hemagglutination buffer pH 7.2, 0.05% w/v bovine serum albumin) was then added. The plates were covered and incubated 30 min. at 37° C. The blocking buffer was discarded by inversion and manual shaking. Plates were washed twice with hemagglutination buffer (375 μl/well), then once using hemagglutination buffer with 2% w/v trehalose (375 μl/well) (Fluka, Ronkonkoma, N.Y.). Plates were vigorously tapped dry manually and then dried for approximately 4 hr. under vacuum at ≦0.5 Torr at 25° C., sealed in mylar pouches with desiccant, and stored overnight at room temperature prior to use. The plates were stored thereafter at 2°–8° C.

SDA reactions (50 μl) in microcentrifuge tubes were mixed with 5 μl of 1 mg/ml carrier DNA (sheared by sonication) (salmon sperm, Sigma, St. Louis, Mo.). The samples were heated for 5 min. at 95° C. to denature DNA and allowed to cool at room temperature for 5 min. Forty-five μl of hybridization mixture (0.5M sodium phosphate pH 7, 0.1% w/v bovine serum albumin (Sigma, St. Louis, Mo.), 2 pmole biotinylated capture oligodeoxynucleotide probe, and 0.5–1 pmole AP detector oligodeoxynucleotide probe was added per sample for a final volume of 100 μl. The samples were incubated for 5 min. at 37° C. to hybridize DNA. Individual samples were added to each coated microtiter plate well, covered, and incubated for 30 min. at 37° C. Three stringency washes (300 μl/well) (10 mM sodium phosphate pH 7, 0.1% w/v bovine serum albumin, 0.05% v/v NONIDET 40) were performed at room temperature. Each wash was allowed to remain in the microtiter wells for 1 min. before removing. LUMIPHOS 530 (100 μl) (Lumigen, Inc., Detroit, Mich.) substrate was added, and the plates were covered and incubated for 30 min. at 37° C. Luminescence was read in Relative Light Units (RLU) on a microtiter plate luminometer (Labsystems, Research Triangle Park, N.C.) at 37° C., using a 2 sec./well integration time.

All treatments produced more amplified target than could be detected by the luminometer (i.e., over 20,000 RLUs). This demonstrated that the washing protocols removed inhibitory compounds introduced during processing that would otherwise completely inhibit SDA. A comparison of the RLUs obtained from a standard curve of M.tb genomic DNA amplifications indicated that 20,000 RLUs were equivalent to approximately 50 M.tb genomes, indicating that at least 50 organisms were detected in each sample. Comparison of the data obtained from amplification of 2.5 μl versus 25 μl of sample showed that the amplification and detection of the IS6110 target sequence produced chemiluminescent signals that were still beyond the dynamic range of the luminometer. Therefore, although the inventive processing methods were highly successful, the efficiency of the wash could not be quantitatively determined from the amplification of M.tb target.

However, when 2.5 μl of sample were introduced into SDA, amplification and detection of the internal control sequence produced a mean value of 5,609 RLUs (N=16, SD=840) whereas 25 μl of sample gave 1,864 mean RLUs (N=28, SD=1206). This indicated that the amplification efficiency of reactions containing 25 μl of sample was reduced three fold as compared to reactions containing 2.5 μl. Throughout these experiments, analysis of the internal control "signature" sequence proved to be a more reliable indicator of inter-sample heterogeneity because it was present at a constant number of copies per sample. It therefore gave a better measure of SDA inhibition. In contrast, M.tb are subject to clumping and were not usually evenly distributed between aliquots.

This experiment demonstrated the feasibility of the wash protocol because M.tb DNA was successfully amplified from TB-positive samples. However, the SDA amplification was not optimal and therefore the wash protocol was further refined as described in the following Examples.

EXAMPLE 2

The feasibility of using microcentrifugation as a means for removing inhibitors from liquified sputum samples was assessed by amplification of M.tb genomic DNA spiked into microcentrifuge-processed samples. This would provide faster sample processing with smaller wash volumes than the clinical centrifuge wash method of Example 1.

Sample liquification was performed according to the protocol recommended by BACTEC. Seven TB-negative clinical sputum samples were pooled in a 200 ml flask (total volume about 50 ml). This was mixed vigorously with an approximately equal volume of 2% NaOH/1.45% citrate/ 0.5% NALC and incubated for 20 min. at room temperature. The sample was aliquoted into ten 50 ml disposable tubes. Each aliquot was brought to 50 ml with neutralizing buffer, then centrifuged for 20 min. at 4,200xg. The resulting NALC pellets were pooled in order to make a homogeneous sample from which aliquots for microcentrifuge washing could be tested. From this pooled NALC pellet the following aliquots were prepared: I. Six 0.15 ml aliquots in 50 ml disposable tubes, and II. Twenty-four 0.15 ml aliquots in 1.5 ml disposable screw-cap microcentrifuge tubes.

The sample groups were processed as follows. The aliquots in 50 ml tubes were washed twice with 20 ml of 25 mM $KPO_4$ in a clinical centrifuge as in Example 1. These samples were positive controls, as Example 1 demonstrated that this method successfully removes inhibitors. Aliquots in microcentrifuge tubes were processed as follows:

A. Two washes in 1 ml 25 mM $KPO_4$ with microcentrifugation, 1 min. each.

B. Three washes in 1 ml 25 mM $KPO_4$ with microcentrifugation, 1 min. each.

C. Two washes in 1 ml 25 mM $KPO_4$ with microcentrifugation, 5 min. each.

D. Three washes in 1 ml 25 mM $KPO_4$ with microcentrifugation, 5 min. each.

E. Two washes in 20 ml 25 mM $KPO_4$ with clinical centrifugation, 5 min. each. (i.e., as in Example 1).

After washing, the pellets were resuspended in 250 µl of $KPO_4$, vortexed, autoclaved and microfuged for 1 min. The microcentrifuge-produced pellets were tighter than the clinical centrifuge pellets and were aspirated with a pipet tip to resuspend. The resulting supernatants were each spiked with 25 copies of M.tb genomic DNA and subjected to SDA with co-amplification of an internal control sequence and chemiluminescent detection as in Example 1. All of the samples containing M.tb genomic DNA showed successful amplification, demonstrating that microcentrifugation is a successful method for washing clinical samples to remove amplification inhibitors and that the method is compatible with the BACTEC liquification protocol.

The mean RLUs of IS6110 amplification were similar for the various sample processing methods:

| PROCESS | RLUs | SD |
|---|---|---|
| A | 3,150 | 1,339 |
| B | 3,235 | 1,016 |
| C | 2,770 | 1,506 |
| D | 2,465 | 575 |
| E | 2,107 | 1,469 |

An F test (as according to Sokal, R. R. and Rohlf, F. J. 1969. *Biometry*, W. H. Freeman, San Francisco) indicated the differences between these treatments were not significant. Therefore, using a microcentrifuge gave data equivalent to the clinical centrifuge wash protocol, but with the advantage that it was a faster and less cumbersome method.

The mean RLUs of the amplified internal control sequence suggested that the use of two microcentrifuge washes gave higher amplification than the other treatments:

| PROCESS | RLUs | SD |
|---|---|---|
| A | 1,756 | 1,025 |
| B | 736 | 144 |
| C | 793 | 568 |
| D | 756 | 479 |
| E | 454 | 369 |

An F test (as according to Sokal and Rohlf, supra) indicated that there was a significant difference between the treatments at the $p=0.05$ level.

This experiment indicated the feasibility of the method but showed high variability between samples. As high variability may have resulted in the lack of significant differences in IS6110 amplification with the various treatments, further experiments were run to validate the use of microfuge washes with TB-positive clinical samples and reduce the variability. These experiments are described below.

EXAMPLE 3

Example 2 was repeated using TB-positive clinical sputum samples to determine if microcentrifugation could be a replacement or alternative for clinical centrifugation for sample washing. This would allow smaller volumes of wash solution to be used, with shorter processing times. A TB-positive and a pooled TB-negative clinical sputum sample were processed through the neutralization and first concentration step of the BACTEC protocol by clinical centrifugation. Samples were then washed by either the standard procotol (further clinical centrifugation) or microcentrifugation.

One TB-positive and ten TB-negative samples were liquified separately, neutralized and centrifuged in a clinical centrifuge at 4,200 rpm at 4° C. for 20 min. The supernatants were discarded and the negative sample pellets were resuspended and combined (total volume about 5 ml). Two 250 µl aliquots were transferred to 50 ml tubes and four 250 µl aliquots were transferred to 2 ml screw-cap tubes. The remaining negative pellet was added to the pellet obtained from processing of the positive sample and it was divided in 250 µl aliquots into four 50 ml tubes and eight 2 ml screw-cap tubes. $KPO_4$ (25 mM, pH 7.6) was added to the 50 ml tubes (negative and positive) to a total volume of 20 ml. The samples were mixed and pelleted in a clinical centrifuge for 5 min. at 4° C. The supernatant was decanted and the wash was repeated with another 20 ml of buffer.

These pellets were resuspended in the remaining sample fluid, transferred to 2 ml screw-cap tubes, and capped.

To the 2 ml samples (positive and negative), 1 ml of 25 mM $KPO_4$, pH 7.6 was added. The tubes were mixed and the samples pelleted by microcentrifugation for 5 min. at room temperature. The supernatants were removed with a micropipette. The wash was repeated once on one set of two negatives and one set of two positives and repeated twice on the remaining tubes. The pellets were finally resuspended in 350 µl of $KPO_4$ buffer. The clinical centrifuge samples were similarly adjusted to 350 µl using $KPO_4$ buffer. The tubes were then autoclaved, vortexed briefly and microcentrifuged for 1 min. Supernatants were collected for SDA amplification. Two tubes containing buffer to be spiked with M.tb genomic DNA prior to SDA (positive controls) were also included.

All samples processed by the microcentrifuge method were amplifiable by SDA. Numerous samples amplified to levels above what the luminometer can detect, indicating that sample inhibitors had been removed by the processing method. The results were quite variable, with IS6110 results varying between 3,490 and over 20,000 RLUs. Washing by microcentrifuge gave lower levels of amplification of the control sequence than washing by clinical centrifuge; two microfuge washes produced 2,703 (+/−1,101) RLUs, three washes produced 1,196 (+/−581) RLUs and two clinical centrifuge washes produced 5,867 (+/−1,642) RLUs. These findings and those given in Example 2 suggested that microcentrifugation washes should preferably be limited to 1 min., as 5 min. washes appeared less effective at removing SDA inhibition than washing in the clinical centrifuge. This also implied that longer microcentrifugations gathered more inhibitors in the washed pellets.

EXAMPLE 4

Samples were processed from liquified samples to determine if this was a feasible alternative to splitting the processed pellets. Seven TB-negative sputum samples were mixed and split into two pools—a TB-negative pool and a TB-positive pool into which was mixed a single TB-positive sample. Both sample pools were liquified by the BACTEC-recommended protocol by addition of an equal volume of 2% NaOH/1.45% sodium citrate/0.5% NALC, as in Example 1. After 20 min. at room temperature, each pool was aliquoted as follows. Two aliquots of 10 ml each were centrifuged for 20 min. in a clinical centrifuge at 4,000 x g. The resulting pellets were washed twice in 20 ml 25 mM $KPO_4$ with 5 min. centrifugation in a clinical centrifuge. Four aliquots of 1 ml each were centrifuged in 2 ml microfuge tubes for 5 min. at 13,000 x g in a microcentrifuge. The resulting pellets were washed by two or three successive 1 ml washes in 25 mM $KPO_4$ by microcentrifugation for 1 min. at 13,000 x g.

The final pellets for all samples were resuspended in 300 µl $KPO_4$, then autoclaved. The final samples were microcentrifuged briefly to remove debris and the supernatants were subjected to SDA and detection in the chemiluminescent probe assay. The assay signals for all of the TB-positive samples were over 20,000 RLU, confirming that they are positive and that the method successfully removed inhibitors. Negative samples produced the appropriate level of signal, corresponding to less than one M.tb genome. This confirmed that splitting the sample during liquification, followed by microcentrifugation, is a useful alternative to splitting the NALC pellet. This procedure simplifies parallel processing of a sample for both culture and nucleic acid analysis.

EXAMPLE 5

This experiment demonstrated that the present invention can also be used to process small volumes of raw sputum directly for SDA. This was designated the "micro processing" method. Micro processing of a small aliquot of the sample saves a significant amount of sample processing time as compared to the conventional method of processing of the whole sample. In addition, micro processing allows the remainder of the sample to be stored for later re-testing or culturing, whereas a whole sample processed by the conventional method must be cultured immediately to avoid loss of M.tb viability.

For micro processing, 0.5 ml aliquots of raw sputum were transferred to 2 ml microfuge tubes using a 1 ml pipettor. The disposable plastic pipet tips were cut to widen the bore and bevel the edge in order to facilitate transfer of the viscous samples. Five aliquots were taken from each of two TB-positive samples (determined by culture) and two TB-negative samples. The remainder of the samples (approximately 5 ml) was used for the clinical centrifuge sample processing procedure. These were liquified, concentrated and washed according to the clinical centrifuge sample processing methods described in Examples 3 and 4. The NALC pellets processed by the clinical centrifuge method were split into 5 aliquots.

The aliquots for micro processing were liquified by addition of 0.5 ml of 2% NaOH, 1.45% sodium citrate and 0.5% N-acetyl L-cysteine, then mixed vigorously on a vortex mixer. The samples were microfuged for 5 min. The resulting pellets were given two successive washes with 1 ml 25 mM $KPO_4$ by 1 min. microcentrifugation. The final washed pellets of both sample processing methods were resuspended in 200 µl of the phosphate buffer and lysed by autoclaving. SDA was performed on the samples with co-amplification of 25,000 copies of the internal control sequence as previously described.

The results of amplification confirmed that the micro processing method had advantages for the preparation of amplification-compatible samples. In addition to the significantly shortened processing time and ability to do the sample processing in a biological safety cabinet, M.tb DNA amplified from the positive micro processed samples gave higher levels of signal than positive samples processed by the clinical centrifuge method:

| PROCESS | TB | RLUs | SD |
| --- | --- | --- | --- |
| BACTEC pellet wash | + | 4,897 | 3,355 |
| BACTEC pellet wash | − | 123 | 102 |
| Micro processed | + | 14,624 | 5,451 |
| Micro processed | − | 317 | 108 |

Likewise, amplification of the internal control sequence from micro processed samples gave higher RLUs than the clinical centrifuge processing method:

| PROCESS | RLUs | SD |
| --- | --- | --- |
| BACTEC pellet wash (TB + and −) | 301 | 184 |
| Micro processed (TB + and −) | 1,282 | 849 |

The micro processing method therefore appeared to be a useful method for preparing SDA-compatible samples when culturing was not also required.

EXAMPLE 6

The following is a preferred embodiment of the micro-processing method of the invention for use when both nucleic acid analysis and culturing of a single sample are desired. Time and handling were minimized by using microcentrifuge washes. SDA variability was minimized by: 1) reducing wash time to 1 min.; 2) lysing/disinfecting samples in a boiling water bath, and 3) increasing the final volume of the processed sample to 1 ml.

Three sputum samples, judged TB-positive by acid fast staining and microbiological culture, and three TB-negative sputum samples were processed through the liquification, neutralization and concentration steps of the BACTEC protocol by clinical centrifugation. Each processed pellet was split into four aliquots which were transferred into 2 ml microfuge tubes. Each aliquot received 1 ml of 25 mM $KPO_4$, was mixed on a vortex mixer, and was microfuged for 1 min. Supernatants were discarded and the wash was repeated. The final washed pellets were each resuspended in 1 ml of 25 mM $KPO_4$. M.tb in the samples was lysed by submerging the samples in a boiling water bath for 30 min. Twenty-five µl of each sample were then subjected to co-amplification of the internal control sequence and M.tb IS6110 target DNA by SDA. Amplification products were detected in the chemiluminescence assay previously described. Increasing the final sample volume to 1 ml and using a boiling water bath instead of autoclaving appeared to contribute to improved reproducibility in the amplification reaction.

The assay signals from positive samples ranged from 13,447 to 20,000 RLUs, the limit of the luminometer. Negative samples produced mean RLUs of 361 (+/−432), equal to zero on the standard curve. This indicated that the TB-positive samples could be clearly differentiated from the negative samples. The RLU values of the internal control sequence indicated that the samples were not inhibitory and that variability between the samples was low:

| | | INTERNAL CONTROL SEQUENCE | | |
|---|---|---|---|---|
| SAMPLE # | TB | MEAN RLUs | SD | % CV |
| 7960 | negative | 5,072 | 640 | 13 |
| 9646 | negative | 5,415 | 386 | 7 |
| 9815 | negative | 5,414 | 1,186 | 22 |
| 147 | positive | 4,830 | 110 | 7 |
| 205 | positive | 4,118 | 431 | 3 |
| 522 | positive | 4,224 | 565 | 3 |
| Control | Buffer + IS6110 | 4,511 | 1,056 | 23 |

These data indicated that the wash protocol rendered the samples completely noninhibitory to SDA, thereby allowing efficient amplification of the M.tb DNA. It also demonstrated that the processing technique was highly reproducible.

---

What is claimed is:

1. A method for processing *Mycobacterium tuberculosis* consisting essentially of:

a) liquifying a sputum sample;

b) centrifuging the liquified sample to form a liquified pellet;

c) washing the liquified pellet two or three times with a wash solution consisting of saline, water or a buffer which does not contain detergents, enzymes or chelating agents, and centrifuging between washes at a speed sufficient to form a washed pellet which is resistant to loss of material during washing, and;

d) resuspending the washed pellet in a solution consisting of saline, water or a buffer which does not contain detergents, enzymes or chelating agents and lysing the *Mycobacterium tuberculosis,* if present, by heating at 95°–120° C. for about 5–30 minutes.

2. The method according to claim 1 further comprising amplification of a target nucleic acid sequence released by lysis of the *Mycobacterium tuberculosis*.

3. The method according to claim 2 wherein the washed pellet is resuspended in $KPO_4$ buffer and the target nucleic acid sequence is amplified by Strand Displacement Amplification.

4. The method according to claim 3 wherein the pellet is washed with about 20 ml of wash solution and centrifuged at a minimum of about 4,000 xg for at least 5 minutes.

5. The method according to claim 3 wherein the target nucleic acid sequence amplified is IS6110.

6. The method according to claim 1 wherein the sputum sample is liquified by treatment with a reagent comprising NaOH, sodium citrate and N-acetyl L-cysteine.

7. The method according to claim 3 wherein the pellet is washed with at least 1 ml of wash solution and centrifuged at a minimum of about 12,000 xg for at least 1 minute.

8. The method according to claim 3 wherein a first portion of the liquified pellet is washed and lysed after liquification and a second portion of the liquified pellet is cultured after liquification.

9. The method according to claim 8 wherein the washed pellet is washed with at least 1 ml of wash solution and centrifuged at a minimum of 12,000 xg for at least 1 minute.

10. A method for processing *Mycobacterium tuberculosis* consisting essentially of:
   a) liquifying a sputum sample;
   b) centrifuging the liquified sample to form a liquified pellet;
   c) washing the pellet two or three times in saline, water or a buffer which does not contain detergents, enzymes or chelating agents, centrifuging between washes at at least 12,000 xg to form a washed pellet which is resistant to loss of material during washing, and;
   d) resuspending the washed pellet in at least 1 ml of saline, water or a buffer which does not contain detergents, enzymes or chelating agents and lysing the *Mycobacterium tuberculosis*, if present, by heating in a boiling water bath for about 5–30 minutes.

11. The method according to claim 10 wherein a target nucleic acid sequence released by lysis of the *Mycobacterium tuberculosis* is amplified*.

12. The method according to claim 11 wherein the washed pellet is resuspended in $KPO_4$ buffer and the target nucleic acid sequence is amplified by Strand Displacement Amplification.

13. The method according to claim 12 wherein the target nucleic acid sequence amplified is IS6110.

14. The method according to claim 10 wherein the sputum sample is liquified by treatment with NaOH, sodium citrate and N-acetyl L-cysteine.

15. The method according to claim 12 wherein a first portion of the liquified pellet is washed and lysed after liquification and a second portion of the liquified pellet is cultured after liquification.

* * * * *